United States Patent
Satou

(10) Patent No.: US 9,651,517 B2
(45) Date of Patent: May 16, 2017

(54) CERAMIC HEATER AND GAS SENSOR ELEMENT USING THE SAME

(71) Applicant: DENSO CORPORATION, Kariya, Aichi-pref. (JP)

(72) Inventor: Chimato Satou, Kariya (JP)

(73) Assignee: DENSO CORPORATION, Kariya (JP)

( * ) Notice: Subject to any disclaimer, the term of this patent is extended or adjusted under 35 U.S.C. 154(b) by 244 days.

(21) Appl. No.: 14/617,038

(22) Filed: Feb. 9, 2015

(65) Prior Publication Data

US 2015/0226696 A1 Aug. 13, 2015

(30) Foreign Application Priority Data

Feb. 11, 2014 (JP) ................. 2014-023932

(51) Int. Cl.
*G01N 27/27* (2006.01)
*G01N 27/406* (2006.01)
*H05B 3/10* (2006.01)
*H05B 3/26* (2006.01)

(52) U.S. Cl.
CPC .......... *G01N 27/4067* (2013.01); *H05B 3/10* (2013.01); *H05B 3/262* (2013.01)

(58) Field of Classification Search
CPC ....... G01N 27/4067; H05B 3/262; H05B 3/10
See application file for complete search history.

(56) References Cited

U.S. PATENT DOCUMENTS

| 4,639,305 A | 1/1987 | Shibata et al. |
|---|---|---|
| 5,895,591 A | 4/1999 | Kojima et al. |
| 6,194,693 B1 | 2/2001 | Shirai et al. |
| 6,236,028 B1 | 5/2001 | Shirai et al. |
| 6,261,429 B1 | 7/2001 | Jach et al. |
| 2001/0050280 A1 | 12/2001 | Yamada et al. |
| 2007/0264529 A1 | 11/2007 | Wahl et al. |
| 2009/0250344 A1 | 10/2009 | Ohya et al. |
| 2015/0001077 A1* | 1/2015 | Oya ................ H05B 3/265 204/424 |

FOREIGN PATENT DOCUMENTS

| JP | UM S62-167396 | 10/1987 |
|---|---|---|
| JP | H08-148260 | 6/1996 |
| JP | H11-157920 | 6/1999 |
| JP | 2000-268944 | 9/2000 |
| JP | 2004-006345 | 1/2004 |
| JP | 2005-310554 | 11/2005 |

* cited by examiner

*Primary Examiner* — Arun S Phasge
(74) *Attorney, Agent, or Firm* — Nixon & Vanderhye P.C.

(57) ABSTRACT

A ceramic heater has a plate substrate made of ceramic and a conductive layer. The conductive layer has a heating section and a pair of lead sections. When receiving electric power, the conductive layer generates heat. The lead sections are formed at one section on the plate substrate adjacent to each other in a width direction and formed along a longitudinal direction on the plate substrate. The heating section is formed to meander on the other section in the plate substrate and both ends of the heating section are connected to the lead sections, respectively. In particular, central sections formed at a central area of the heating section in the width direction and the longitudinal direction have a resistance value which is lower per unit length than a resistance value of other linear shaped sections of the heating section.

7 Claims, 5 Drawing Sheets

CERAMIC HEATER AND GAS SENSOR ELEMENT USING THE SAME

CROSS-REFERENCE TO RELATED APPLICATION

This application is related to and claims priority from Japanese Patent Application No. 2014-23932 filed on Feb. 11, 2014, the contents of which are hereby incorporated by reference.

BACKGROUND OF THE INVENTION

1. Field of the Invention

The present invention relates to ceramic heaters and gas sensor elements using the ceramic heater. In particular, the ceramic heater has a structure in which a conductive layer is formed on a plate shaped base member made of ceramic.

2. Description of the Related Art

Ceramic heaters are widely used to various applications which are required to generate heat in order to quickly increase a temperature of a target section. For example, a ceramic heater is used to a gas sensor to be mounted on an exhaust gas pipe connected to an internal combustion engine. When receiving electric power, the ceramic heater generates and supplies heat to a solid electrolyte body in a gas sensor in order to speedily increase a temperature of the solid electrolyte body and a pair of electrodes formed on the solid electrolyte body so that the temperature of the solid electrolyte and the electrodes quickly reach an activation temperature thereof.

For example, a patent literature 1, Japanese patent laid open publication number S62-167396, shows a ceramic heater having a heating resistance pattern formed on a heat resistance ceramic substrate so that a central section and both end sections of the heating resistance pattern have a different line width or a different line thickness in order to approximately have a uniform temperature distribution thereof. In particular, the heating resistance pattern has a structure in which the linear shaped central section has the line width which is larger than a line width of the both end sections. Booth end sections become a low heating temperature which is lower than that of the central section in the heating resistance pattern.

By the way, because the recent vehicle emissions control of reducing motor vehicle emissions, etc. is becoming stricter year by year in view of environmental protection, there is a demand to turn off electric power to be supplied to in-vehicle electronic devices such as a gas sensor during an idling stop control. However, when a ceramic heater in a gas sensor is repeatedly turning on and off, the ceramic heater is repeatedly expanded and contracted. This deteriorates the heating section in the ceramic heater and there is a possible reduction of a product life of the ceramic heater.

SUMMARY

It is therefore desired to provide a ceramic heater and a gas sensor element equipped with the ceramic heater having a long product life capable of suppressing deterioration of a heating section of the ceramic heater An exemplary embodiment provides a ceramic heater having a plate substrate made of ceramic and a conductive layer configured to generate heat when receiving electric power. In the ceramic heater, the conductive layer has a pair of lead sections and a heating section. The lead sections are formed on a first section of the plate substrate. The lead sections are formed on a first section of the plate substrate extending in a longitudinal direction L (or a lateral direction, see FIG. 1) of the plate substrate and adjacent in a width direction W to the longitudinal direction on the plate substrate. The longitudinal direction is perpendicular to the width direction on the plate substrate. The heating section is formed on the plate substrate to meander so that end sections of the heating section are connected to respective lead sections on a second section along the longitudinal direction of the plate substrate. The heating section has linear shaped sections formed at a central section in the width direction and the longitudinal direction of the plate substrate. The linear shaped sections formed at the central section have a first resistance value per unit length which is lower than a second resistance value per unit length of linear shaped sections formed on the other sections except for the central section.

In accordance with another exemplary embodiment, there is provided a gas sensor element equipped with the ceramic heater according to the exemplary embodiment having the structure previously described. In particular, the gas sensor element has a solid electrolyte body having oxygen ion conductivity laminated with the ceramic heater. A target gas chamber is formed on a first surface of the solid electrolyte body and a reference gas chamber is formed on a second surface of the solid electrolyte body. The gas sensor element further has a pair of electrodes. The electrodes are formed on the first surface and the second surface of the solid electrolyte body, respectively. The electrodes detect an oxygen concentration in a target gas introduced into the target gas chamber. The central sections of the inner linear shaped sections of the heating section are formed along the longitudinal direction so that the central sections of the inner linear shaped sections face the electrodes.

In the ceramic heater having the improved structure previously described, the heating section generates heat when receiving electric power. In particular, the central linear shaped sections have a maximum temperature as compared with a temperature of the other linear shaped sections in the heating section. In order to avoid this drawback, the ceramic heater according to the exemplary embodiment has the improved structure in which the central linear shaped sections have a resistance value per unit length which is lower than a resistance value of each of the other linear shaped sections. This improved structure makes it possible to decrease a peak temperature value of the central linear shaped section when the heating section receives electric power and generates heat. In more detail, the central linear shaped sections are formed at the central section in the longitudinal direction and inside in the width direction of the heating section. The central linear shaped sections have a resistance value per unit length which is lower than a resistance value of the other linear shaped sections. The other linear shaped sections are formed at both sides of the heating section in the longitudinal direction and outside in the width direction of the heating section.

This improved structure of the ceramic heater makes it possible to decrease the peak temperature at the central linear shaped sections formed at the central section in the longitudinal direction and the width direction of the heating section when the heating section generates heat by receiving electric power. This improved structure makes it possible to suppress deterioration of the heating section even if turning on and off of electric power is repeated in the ceramic heater through the lead sections and a repetition of expansion and shrinkage occurs in the inside of the ceramic heater. Further, because this improved structure makes it possible to suppress deterioration of the heating section, it is possible for the ceramic heater to have a long life. Still further, when a gas sensor element uses the ceramic heater having the improved structure previously described, the gas sensor element has a long life.

BRIEF DESCRIPTION OF THE DRAWINGS

A preferred, non-limiting embodiment of the present invention will be described by way of example with reference to the accompanying drawings, in which.

DETAILED DESCRIPTION OF THE PREFERRED EMBODIMENTS

Figure 1:
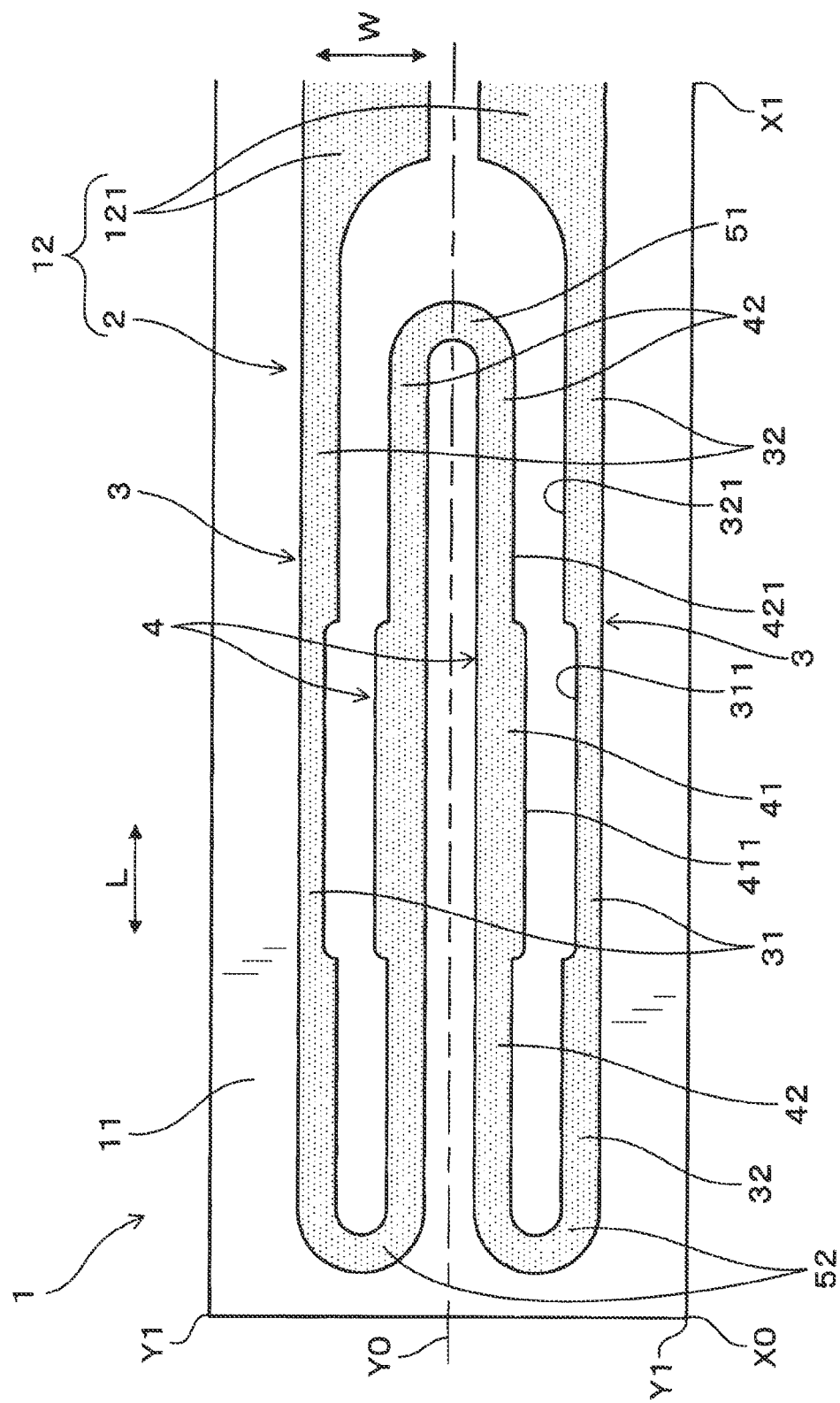
FIG. 1 is a view explaining a conductive layer formed on a plate substrate in a ceramic heater according to an exemplary embodiment of the present invention.

Hereinafter, various embodiments of the present invention will be described with reference to the accompanying drawings. In the following description of the various embodiments, like reference characters or numerals designate like or equivalent component parts throughout the several diagrams.

A description will be given of a structure of a ceramic heater and a gas sensor element equipped with the ceramic heater according to an exemplary embodiment of the present invention.

In the structure of the ceramic heater according to the exemplary embodiment, the linear shaped section indicates sections having a width and a line in a heating section formed in the ceramic heater. The central section indicates sections except for both end sections in the heating section.

The heating section has the improved structure as follows. A pair of outer linear shaped sections is formed on the plate substrate along the longitudinal direction L (or the lateral direction) of the ceramic heater and at the outer of the plate substrate. A pair of inner linear shaped sections is formed on the plate substrate parallel to the outer linear shaped sections and inside of the outer linear shaped sections as viewed in the width direction. First end sections (see at the right side in FIG. 1) of the inner linear shaped sections are connected together. A second end section (see at the left side in FIG. 1) of each of the outer linear shaped sections is connected to a second end section (see at the left side in FIG. 1) of each of the inner linear shaped sections in order to form the heating section.

It is preferred for the heating section to have the structure in which a central section of each of the inner linear shaped sections has a resistance value per unit length in the longitudinal direction L, which is lower than a resistance value per unit length in the longitudinal direction L of each of both end sections of the inner linear shaped sections and a resistance value per unit length in the longitudinal direction L of each of the outer linear shaped sections.

This improved structure makes it possible to decrease a peak temperature of the central section of the inner linear shaped sections because the central section in the longitudinal direction of the inner linear shaped sections has a resistance value per unit length which is lower than a resistance value of the other linear shaped sections of the inner linear shaped sections and the outer linear shaped sections.

It is acceptable that the central section of each of the outer linear shaped sections has a resistance value per unit length in the longitudinal direction L which is higher than a resistance value per unit length in the longitudinal direction L of the other section in each of the outer linear shaped sections.

In this structure, the central section in the longitudinal direction L of the outer linear shaped sections has a resistance value which is higher than a resistance value of the central section in the longitudinal direction L of the inner linear shaped sections, where the central section of each of the outer linear shaped sections faces the central section of each of the inner linear shaped sections.

Further, this structure makes it possible to provide the following feature. As compared with a resistance value per unit length of the other sections in the inner linear shaped sections and the outer linear shaped sections, the central section of the inner linear shaped sections has a low resistance value per unit length in the longitudinal direction L, and the central section of the outer linear shaped sections has a high resistance value per unit length in the longitudinal direction L. This improved structure makes it possible to effectively decrease a peak temperature of the central sections of the heating sections in the ceramic heater.

Still further, it is acceptable that the heating section is made of a same conductive material and has a same thickness in order for each of the outer linear shaped sections and the inner linear shaped sections to have a different width in order to have a different resistance value.

It is possible for each of the linear shaped sections including the central sections in the heating section to have a different resistance value per unit length in the longitudinal direction L by adjusting a cross sectional area or using a different material. There are two methods of changing the cross sectional area of each of the linear shaped sections, one method changes a width of each of the linear shaped sections containing the central sections, and the other method changes a thickness of each of these linear shaped sections containing the central sections. In particular, the former method, which changes the width of each section, makes it possible to more easily change the resistance value per unit length.

EXEMPLARY EMBODIMENT

A description will now be given of an exemplary embodiment of the ceramic heater 1 and the gas sensor element 6 equipped with the ceramic heater 1 with reference to the drawings.

FIG. 1 is a view explaining a conductive layer 12 formed on the plate substrate 11 in the ceramic heater 1 according to the exemplary embodiment.

As shown in FIG. 1, the ceramic heater 1 according to the exemplary embodiment has the plate shaped substrate 11 made of ceramic and the conductive layer 12. When receiving electric power, the conductive layer 12 generates heat. The conductive layer 12 has a pair of the lead sections 121 (lead wires) and the heating section 2. The lead sections 121 are formed adjacent to each other in the width direction W (see FIG. 1) which is perpendicular to the longitudinal direction L (or the lateral direction) of the ceramic heater 1. That is, the lead sections 121 are formed along the longitudinal direction L of the ceramic heater 1. The heating section 2 is formed along the longitudinal direction L to meander in the other section on the plate substrate 11 of the ceramic heater 1, where no lead wire is formed. Both the end sections of the heating section 2 are connected to the lead sections 121, respectively.

As shown in FIG. 1, the heating section 2 has central linear shaped sections 31, 41 and other linear shaped sections 32 and 42. The central linear shaped sections 41 are formed at a central section in the heating section 2 along the longitudinal direction L and the width direction W. The central linear shaped sections 31 are formed at a central section in the heating section 2 along the longitudinal direction L and the width direction W.

The central linear shaped section 41 has a resistance value per unit length in the longitudinal direction L which is lower than a resistance value per unit length in the longitudinal direction L of the linear shaped sections 31, 32 and 42.

A description will now be given of the gas sensor element 6 equipped with the ceramic heater 1 having the improved structure previously described with reference to FIG. 1 to FIG. 6.

Figure 2:
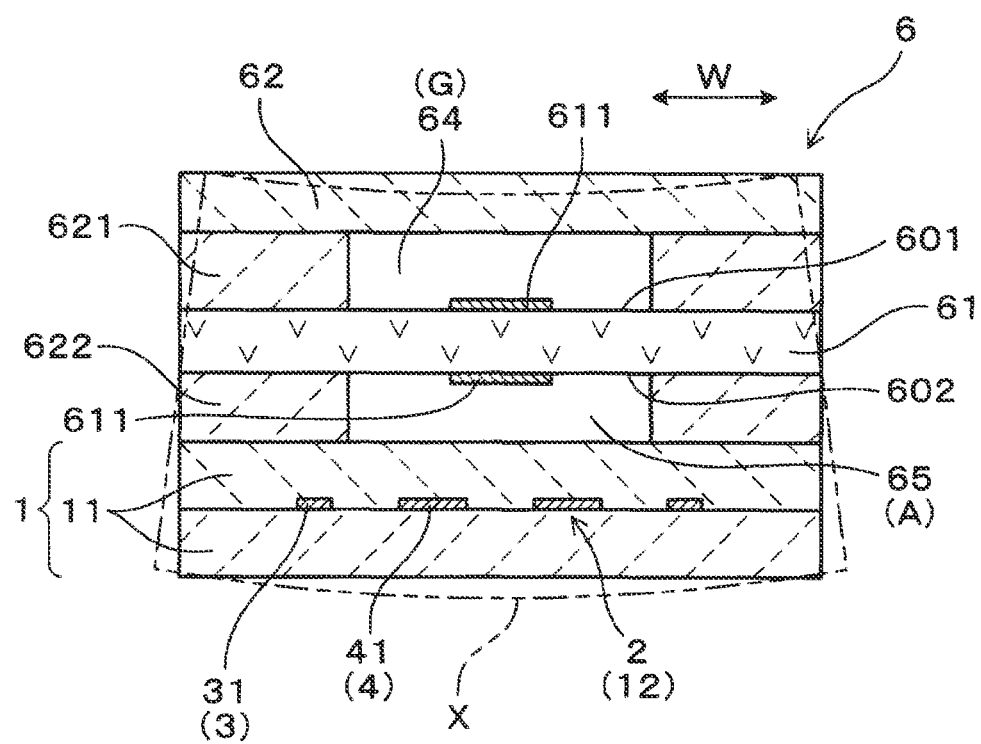
FIG. 2 is a view showing a cross section of a gas sensor element equipped with the ceramic heater according to the exemplary embodiment of the present invention in a width direction which is perpendicular to a longitudinal direction (or a lateral direction) of the gas sensor element.
Figure 3:
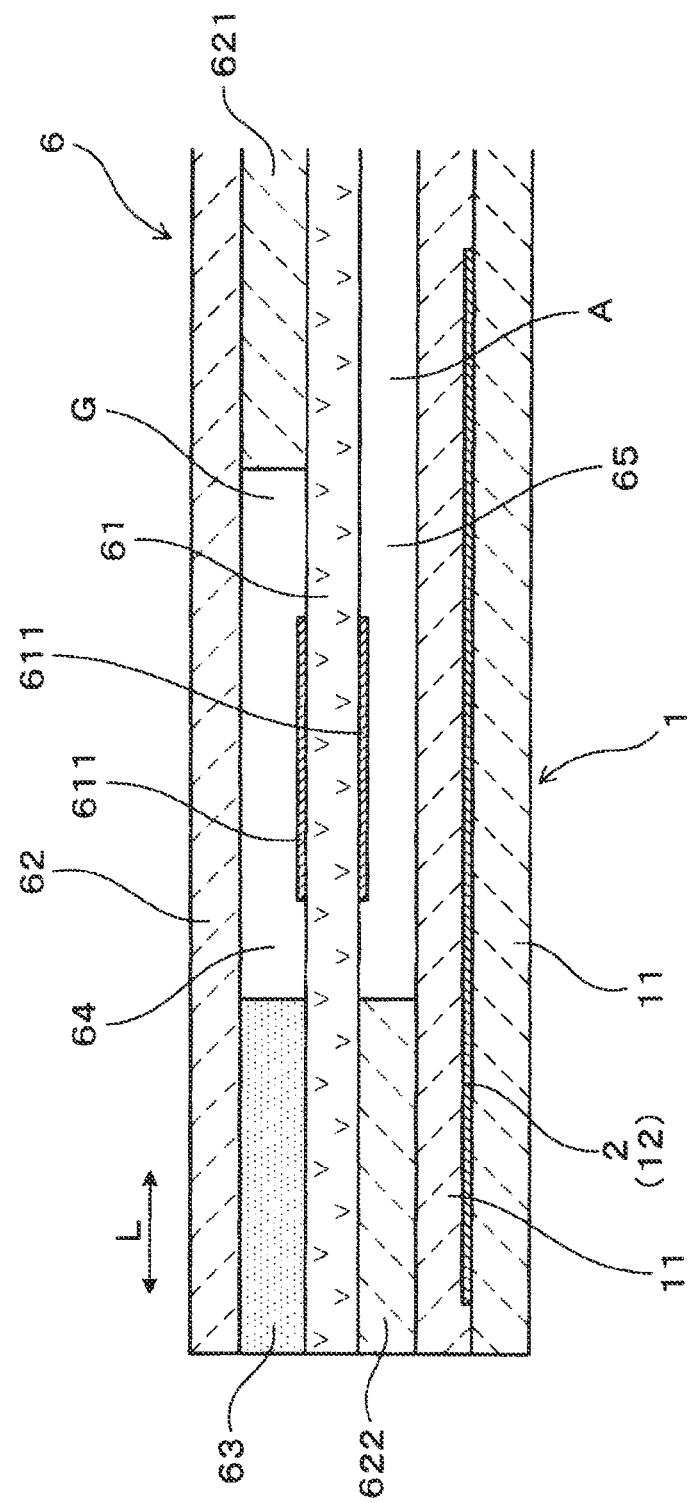
FIG. 3 is a view showing a cross section of the gas sensor element equipped with the ceramic heater according to the exemplary embodiment of the present invention in the longitudinal direction of the gas sensor element.

FIG. 2 is a view showing a cross section of the gas sensor element 6 equipped with the ceramic heater 1 according to the exemplary embodiment, along the width direction W which is orthogonal to the longitudinal direction L of the gas sensor element 6. FIG. 3 is a view showing a cross section of the gas sensor element 6 equipped with the ceramic heater 1 according to the exemplary embodiment in the longitudinal direction L of the gas sensor element 6.

As shown in FIG. 2 and FIG. 3, the ceramic heater 1 according to the exemplary embodiment is used in the gas sensor element 6. The gas sensor element 6 has a structure in which the gas sensor element 6 is laminated in a solid electrolyte body 61. The solid electrolyte body 61 has oxygen ion conduction characteristics.

A target gas chamber 64 is formed on a first surface 601 of the solid electrolyte body 61. A target gas G such as exhaust gas emitted from an internal combustion engine to be measured is introduced into the inside of the target gas chamber 64.

On the other hand, a reference gas chamber 65 is formed on a second surface 602 of the solid electrolyte body 61. A reference gas A such as atmosphere or air is introduced into the inside of the reference gas chamber 65.

The target gas chamber 64 is formed between the first surface 601 of the solid electrolyte body 61 and an insulation layer 62 through an insulation spacer layer 621 formed on the first surface 601 of the solid electrolyte body 61.

The reference gas chamber 65 is formed between the second surface 602 of the solid electrolyte body 61 and the ceramic heater 1 through an insulation spacer layer 622. That is, as shown in FIG. 2, the insulation spacer layer 622 and the reference gas chamber 65 are formed on the ceramic heater 1, and the solid electrolyte body 1 is formed on the insulation spacer layer 622, and the insulation spacer layer 621 is formed on the solid electrolyte body 61.

As shown in FIG. 3, a porous diffusion resistance layer 63 is formed at a front end section of the first surface 601 of the solid electrolyte body 61 in order to introduce the target gas G into the target gas chamber 64 through the porous diffusion resistance layer 63.

As shown in FIG. 2 and FIG. 3, a pair of electrodes 611 is formed on the first surface 601 and the second surface 602, respectively, in order to detect a concentration of oxygen (oxygen concentration) contained in the target gas G. In more detail, the electrode 611 is formed on the first surface 601 of the solid electrolyte body 61, and the other electrode 611 is formed on the second surface 602 of the solid electrolyte body 61.

As shown in FIG. 2 and FIG. 3, the ceramic heater 1 has a structure in which a conductor layer 12 is formed between a pair of plate substrates 11. The gas sensor element 6 equipped with the ceramic heater 1 and the solid electrolyte body 61 has a longitudinal shape extending to the longitudinal direction L.

When electric power is supplied (i.e., the ceramic heater 1 is turned on) and halted (i.e., the ceramic heater 1 is turned off), the ceramic heater 1 is expanded and contracts in a lamination direction of the gas sensor element 6. That is, when the ceramic heater 1 generates heat (electric power is supplied to the conductive layer 12), the gas sensor element 6 is curved in the width direction W (designated with the long dashed double short dashed line in FIG. 2) so that the ceramic heater 1 side has a convex shape in the gas sensor element 6. When the electric power supply is stopped, the gas sensor element 6 is returned to the original shape thereof.

As shown in FIG. 1, the heating section 2 in the ceramic heater 1 according to the exemplary embodiment has a pair of outer linear shaped sections 3 and a pair of inner linear shaped sections 4.

In the ceramic heater 1, the outer linear shaped sections 3 and the inner linear shaped sections 4 are formed parallel to each other along the longitudinal direction L on the plate substrate 11 of the ceramic heater 1. The inner linear shaped sections 4 are formed inside of the outer linear shaped sections 3 as viewed along the width direction W.

As shown in FIG. 1, first end sections (at the right side) of the inner linear shaped sections 4 are connected together through a curved connection section 51. Similarly, second end sections (at the left side) of the outer linear shaped sections 3 are connected to second end sections (at the left side) of the inner linear shaped sections 4 through curved connection sections 52, respectively.

That is, the first end section of each of the outer linear shaped sections 3 and the inner linear shaped sections 4 is located at the right side in which the lead sections 121 are formed in FIG. 1 and the second end section thereof is located at the left side.

Further, lead sections connected to the pair of the electrodes 611 formed on the first and second surfaces 601, 602 of the solid electrolyte body 61 are formed in the first side of the plate substrates 11 in which a pair of the lead sections 121 is formed.

The lead sections 121 and the heating section 2 are formed on the surface of the plate substrate 11 by performing a pattern printing with conductive material. That is, the lead sections 121 and the heating section 2 have the same thickness. The heating section 2 is formed along the longitudinal direction L to meander from one lead section 121 to the other lead section 121. The entire sections of the lead sections 121 and the heating section 2 are made of the same conductive material and have the same thickness. In the structure of the ceramic heater 1 according to the exemplary embodiment, each of the outer linear shaped sections 3 and the inner linear shaped sections 4 has a different resistance value per unit length by changing a width of these outer linear shaped sections 3 and the inner linear shaped sections 4, respectively. The width of each of the outer linear shaped sections 3 and the inner linear shaped sections 4 indicate a width in the width direction of the ceramic heater 1 shown in FIG. 1.

As shown in FIG. 1, in the outer linear shaped sections 3 and the inner linear shaped sections 4 in the heating section 2, each of the linear shaped sections 32 and 42 formed at both sides in the longitudinal direction L has a constant width. On the other hand, each of the central linear shaped sections 41 formed at the central section in the longitudinal direction has a width which is wider than the width of each of the linear shaped sections 32 and 42. Each of the central linear shaped sections 31 formed at the central section in the longitudinal direction L has a width which is narrower than the width of each of the linear shaped sections 32 and 42.

As shown in FIG. 1, the central linear shaped section 41 in each of the inner linear shaped sections 4 has a wide width by expanding the outer surface 411 in the central linear shaped section 41 toward the outer as compared with an outer surface 421 in the linear shaped section 42 in the inner linear shaped sections 4.

On the other hand, the central linear shaped section 31 in each of the outer linear shaped sections 3 has a narrow width by expanding the inner surface 311 in the central linear shaped section 31 toward the outside as compared with an inner surface 321 in the linear shaped section 32 in the outer linear shaped sections 3. An interval between the outer linear shaped section 3 and the inner linear shaped section 4 and an interval between the inner linear shaped section 4 have a constant length.

It is preferable for the ceramic heater 1 to have the structure in which a ratio in width (hereinafter, the width ratio) of the central linear shaped section 41 in each of the inner linear shaped sections 4 to each of the linear shaped sections 32, 42 is within a range of 1.2 to 1.7, and a width ratio of the central linear shaped section 31 in each of the outer linear shaped sections 3 to each of the linear shaped sections 32, 42 is within a range of 0.5 to 0.9 when the width of each of the linear shaped sections 32 and 42 is a value of 1.

When the width ratio of the central linear shaped section 41 to each of the linear shaped sections 32, 42 has an excessively large value, or when the width ratio of the central linear shaped section 31 to each of the linear shaped sections 32, 42 has an excessively small value, deformation is easily generated in the inside of the ceramic heater 1 because the ceramic heater 1 has a large expansion amount or a large shrinkage amount.

In addition, when the width of the central linear shaped section 31 in each of the outer linear shaped sections 3 has a small value, a heating temperature becomes high, and as a result, the central linear shaped section 31 burns out and becomes broken.

When the width of the central linear shaped section 41 in each of the inner linear shaped sections 4 becomes large, there is a possible delay of a temperature rising speed (or an activation speed) of the gas sensor element 6. Accordingly, it is preferable for the ceramic heater 1 to have a structure in which the width ratio of the central linear shaped section 41 to each of the linear shaped sections 32, 42 is within a range of 1.2 to 1.7, and the width ratio of the central linear shaped section 31 to each of the linear shaped sections 32, 42 is within the range of 0.5 to 0.9.

In the ceramic heater 1 according to the exemplary embodiment having the structure previously described, the central linear shaped sections 41 have the maximum width formed at the central section in the heating section 2 of the conductive layer 12. That is, each of the central linear shaped sections 41 has the maximum width and the minimum resistance value per unit length along the longitudinal direction L in the inner linear shaped sections 4 in the ceramic heater 1.

On the other hand, the central linear shaped sections 31 have the minimum width formed at the central section in the heating section 2 of the conductive layer 12. That is, each of the central linear shaped sections 31 has the minimum width and the maximum resistance value per unit length along the longitudinal direction L in the outer linear shaped sections 3 in the ceramic heater 1.

This improved structure makes it possible to effectively decrease a peak temperature of the central section along the longitudinal direction L and the width direction W in the ceramic heater 1 shown in FIG. 1. Further, it is possible to prevent deterioration of the heating section 2 caused by the expansion and shrinkage of the ceramic heater 1 during a repetition of turning on and off to supply electric power to the heating section 2 through the lead sections 121.

The improved structure of the ceramic heater 1 previously described makes it possible to suppress deterioration of the heating section 2 and extend the life time of the ceramic heater 1. Further, because this improved structure can suppress the deterioration of the heating section 2 in the ceramic heater 1, it is possible to extend the life time of the gas sensor element 6 equipped with the ceramic heater 1.

A description will now be given of experimental results regarding a deformation amount at each position on the plate substrate in the longitudinal direction L and the width direction W in the ceramic heater 1 according to the exemplary embodiment and a conventional ceramic heater 9.

Figure 6:
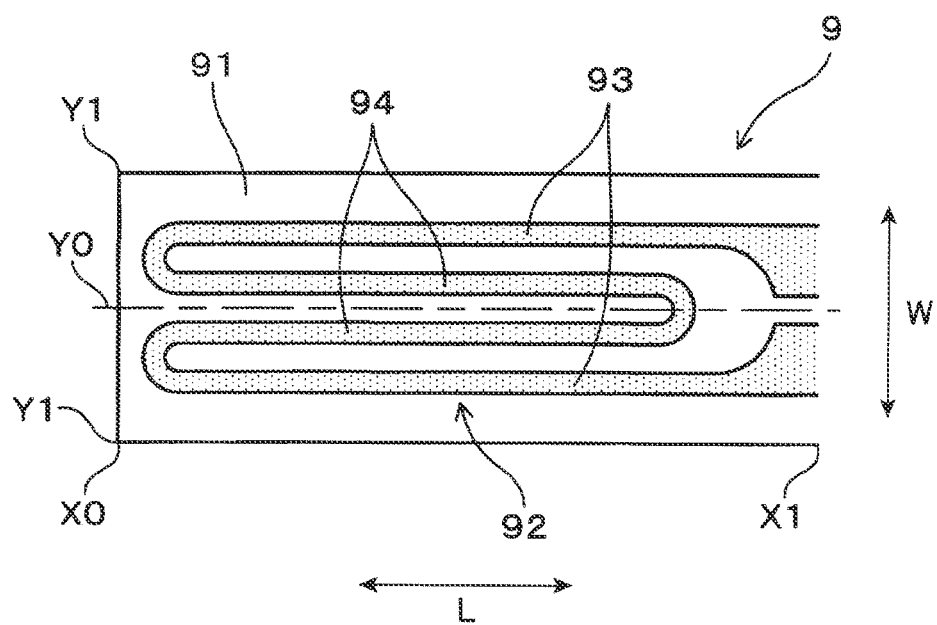
FIG. 6 is a view showing a structure of a conventional ceramic heater having a heating section composed of outer linear shaped sections and inner linear shaped sections.

FIG. 6 is a view showing a structure of the conventional ceramic heater 9 having a heating section 92 formed on a plate substrate 91 composed of outer linear shaped sections 93 and inner linear shaped sections 94.

That is, the outer linear shaped sections 3 and the inner linear shaped sections 4 have a different width, respectively in the ceramic heater 1 according to the exemplary embodiment. On the other hand, the outer linear shaped sections 93 and the inner linear shaped sections 94 have the same width in the conventional ceramic heater 9.

Figure 4:
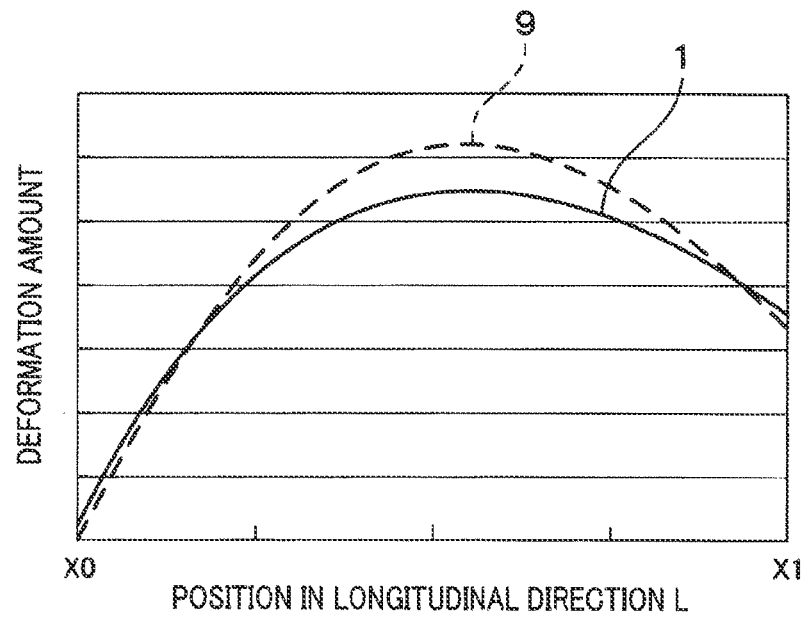
FIG. 4 is a graph schematically showing a change of a deformation amount generated along the longitudinal direction L at the central section in the longitudinal direction W of the heating section in the ceramic heater.

FIG. 4 is a graph schematically showing a change of a deformation amount generated along the longitudinal direction L at the central section in the width direction W of the heating section of the ceramic heater. In FIG. 4, the horizontal axis indicates a position on the plate substrate in the longitudinal direction L of the ceramic heater, and the vertical direction indicates the deformation amount generated at the central section in the width direction W of the plate substrate in the ceramic heater.

In particular, the position X0 in the horizontal axis of FIG. 4 indicates the position of the front end section (see FIG. 1 and FIG. 6) along the longitudinal direction L of each of the ceramic heater 1 according to the exemplary embodiment and the conventional ceramic heater 9. The position X1 in the horizontal axis of FIG. 4 indicates the position of the distal end section (see FIG. 1 and FIG. 6) along the longitudinal direction L in each of the heating section 2 in the ceramic heater 1 according to the exemplary embodiment and the heating section 92 in the conventional ceramic heater 9.

As clearly shown in FIG. 4, the deformation amount generated in each of the ceramic heaters 1 and 9 has the maximum value at the central section in the longitudinal direction L of each of the heating section 2 and 92. Further, the magnitude of the deformation amount in each position corresponds to a temperature of each position in each of the ceramic heater 1 and the conventional heater 9. That is, the more the temperature of the position increases, the more the deformation of the position is increased.

Still further, as compared with the conventional ceramic heater 9, the ceramic heater 1 according to the exemplary embodiment has a peak value of the deformation amount which is lower than the peak value of the deformation amount generated in the conventional ceramic heater 9. This can be understood from the experimental results shown in FIG. 4 that the ceramic heater 1 having the improved structure according to the exemplary embodiment has a low expansion amount and a low shrinkage amount along the longitudinal direction L in the ceramic heater 1 and can suppress deterioration of the heating section 2.

Figure 5:
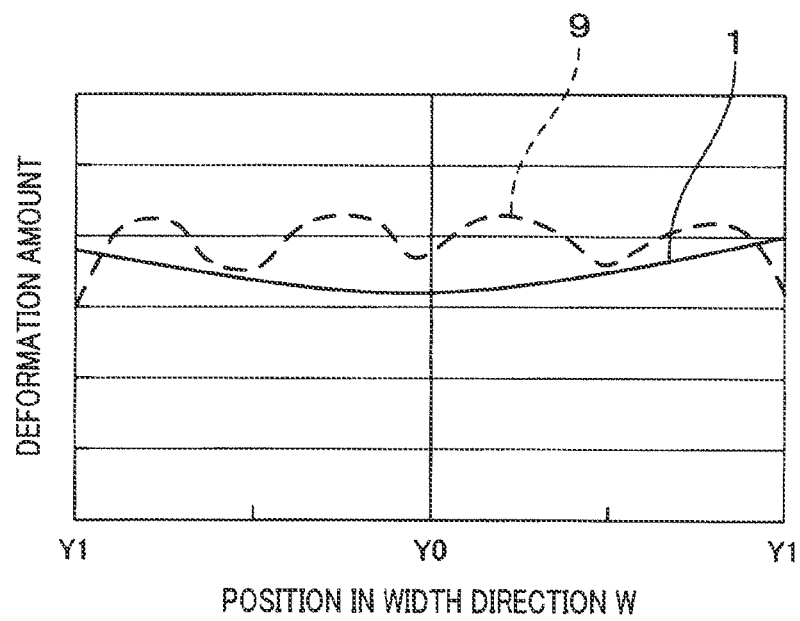
FIG. 5 is a graph schematically showing a change of a deformation amount generated along the width direction W at the central section in the longitudinal direction L of the heating section of the ceramic heater.

FIG. 5 is a graph schematically showing a change of a deformation amount generated along the width direction W at the central section in the longitudinal direction L of the heating section of the ceramic heater. In FIG. 5, the horizontal axis indicates a position on the plate substrate in the width direction W of the ceramic heater, and the vertical direction indicates the deformation amount generated at the central section in the longitudinal direction L of the plate substrate in the ceramic heater.

In particular, the position Y0 in the horizontal axis of FIG. 5 indicates the central position (see FIG. 1 and FIG. 6) along the width direction W of each of the ceramic heater 1 according to the exemplary embodiment and the conventional ceramic heater 9. The position Y1 in the horizontal axis of FIG. 5 indicates the end surface section (see FIG. 1 and FIG. 6) along the width direction W in each of the heating section 2 in the ceramic heater 1 according to the exemplary embodiment and the heating section 92 in the conventional ceramic heater 9.

As shown in FIG. 5, the deformation amount generated in the conventional ceramic heater 9 has a large value at the formation area of the heating section 92 in the width direction W.

On the other hand, the deformation amount generated in the ceramic heater 1 according to the exemplary embodiment has no peak value, i.e., a suppressed value. In other words, the deformation amount generated in the ceramic heater 1 according to the exemplary embodiment changes along a flat curve which approximately has no peak value. It can be understood from the experimental result shown in FIG. 4 and FIG. 5 that the ceramic heater 1 according to the exemplary embodiment can suppress the expansion and shrinkage of the ceramic heater 1 and deterioration of the heating section 2.

While specific embodiments of the present invention have been described in detail, it will be appreciated by those skilled in the art that various modifications and alternatives to those details could be developed in light of the overall teachings of the disclosure. Accordingly, the particular arrangements disclosed are meant to be illustrative only and not limited to the scope of the present invention which is to be given the full breadth of the following claims and all equivalents thereof.

What is claimed is:

1. A ceramic heater comprising:
a plate substrate made of ceramic; and a conductive layer configured to generate heat when receiving electric power, wherein the conductive layer comprises: a pair of lead sections; and a heating section, wherein
the lead sections are formed on a first section of the plate substrate and are adjacent to each other in a width direction which is perpendicular to the longitudinal direction, and
the heating section is formed in a meandering shape in a second section on the plate substrate, and both end sections of the heating section are connected respectively to the lead sections, and
the heating section comprises linear shaped sections formed at a central section in the width direction and the longitudinal direction of the heating section, the linear shaped sections having a first resistance value per unit length which is lower than a second resistance value per unit length of other linear shaped sections formed on the other section outside the central section of the heating section.

2. The ceramic heater according to claim 1, wherein the heating section comprises:
a pair of outer linear shaped sections formed on the plate substrate along the longitudinal direction;
a pair of inner linear shaped sections formed on the plate substrate parallel to the outer linear shaped sections and inner of the outer linear shaped sections in the width direction,
first end sections of the inner linear shaped sections are connected together, and a second end section of each of the outer linear shaped sections is connected to a second end section of each of the inner linear shaped sections in order to form the heating section,
wherein a central section of each of the inner linear shaped sections in the longitudinal direction has a resistance value per unit length which is lower than a resistance value per unit length of each of both end sections of the inner linear shaped sections, and a resistance value per unit length of each of the outer linear shaped sections.

3. A gas sensor element comprising:
the ceramic heater of claim 2; and
a solid electrolyte body having oxygen ion conductivity laminated with the ceramic heater, wherein
a target gas chamber is formed on a first surface of the solid electrolyte body, a reference gas chamber is formed on a second surface of the solid electrolyte body,
a pair of electrodes is formed on the solid electrolyte body, one electrode is formed on the first surface, and the other electrode is formed on the second surface of the solid electrolyte body, and the pairs of electrodes detects an oxygen concentration in a target gas introduced into the target gas chamber, and
the central sections, formed along the longitudinal direction, in the inner linear shaped sections are arranged to face the electrodes.

4. The ceramic heater according to claim 2, wherein a central section of each of the outer linear shaped sections in the longitudinal direction has a resistance value per unit length which is higher than a resistance value per unit length of other section of each of the outer linear shaped sections.

5. The ceramic heater according to claim 2, wherein the heating section is made of a same type of conductive material and has a same thickness, and each of the outer linear shaped sections and the inner linear shaped sections has a different width in order to have a different resistance value.

6. The ceramic heater according to claim 5, wherein a width ratio of the central linear shaped section in each of the inner linear shaped sections to each of the other linear shaped sections is within a range of 1.2 to 1.7, and a width ratio of the central linear shaped section in each of the outer linear shaped sections to each of the other linear shaped sections is within a range of 0.5 to 0.9.

7. A gas sensor element comprising:
the ceramic heater of claim 1; and
a solid electrolyte body having oxygen ion conductivity laminated with the ceramic heater, wherein
a target gas chamber is formed on a first surface of the solid electrolyte body, a reference gas chamber is formed on a second surface of the solid electrolyte body,
a pair of electrodes is formed on the solid electrolyte body, one electrode is formed on the first surface, and the other electrode is formed on the second surface of the solid electrolyte body, and the pairs of electrodes detects an oxygen concentration in a target gas introduced into the target gas chamber, and
the central sections, formed along the longitudinal direction, in the inner linear shaped sections are arranged to face the electrodes.

* * * * *